United States Patent [19]
Charlebois et al.

[11] 4,290,309
[45] Sep. 22, 1981

[54] DIAGNOSTIC ULTRASOUND APPARATUS HAVING AUTOMATIC ISOCENTRIC ROTATOR

[75] Inventors: Thomas F. Charlebois, Oconomowoc, Wis.; Edward J. Roswog, Boston, Mass.

[73] Assignee: General Electric Company, Schenectady, N.Y.

[21] Appl. No.: 122,221

[22] Filed: Feb. 19, 1980

[51] Int. Cl.³ ............................................. G01N 29/04
[52] U.S. Cl. ........................................ 73/621; 73/634
[58] Field of Search ................. 73/621, 634, 619, 633; 128/660

[56] References Cited
U.S. PATENT DOCUMENTS

| | | | |
|---|---|---|---|
| 3,555,888 | 1/1971 | Brown | 73/621 |
| 4,137,777 | 2/1979 | Haverl et al. | 73/633 |
| 4,196,630 | 4/1980 | Rudolph | 73/633 |
| 4,244,227 | 1/1981 | Rudolph et al. | 73/633 |

*Primary Examiner*—Anthony V. Ciarlante
*Attorney, Agent, or Firm*—Wheeler, House, Fuller & Hohenfeldt

[57] ABSTRACT

An ultrasound transducer is translatable for scanning along a body surface by having the transducer mounted at the free end of an articulated arm which is moved in a single nominally vertical plane during a scan. The arm is pivotally connected at one end to a head which is turnable at least about a vertical axis so the arm can be directed in other single planes. The head is mounted on a horizontally and transversely movable arm which is on a longitudinally movable carriage. Potentiometers produce analog signals which allow a microprocessor to determine the difference between the location of the transducer axis and the vertical axis about which the arm swings into different planes. When isocentric rotation is desired, the user locates the transducer over the isocentric point on the body and provides a command signal which, through a servo motor system, causes the transverse arm and longitudinal carriage to move until the vertical head axis is aligned with the transducer. When the arm is swung again, it will positively move in a plane which crosses the isocenter.

3 Claims, 3 Drawing Figures

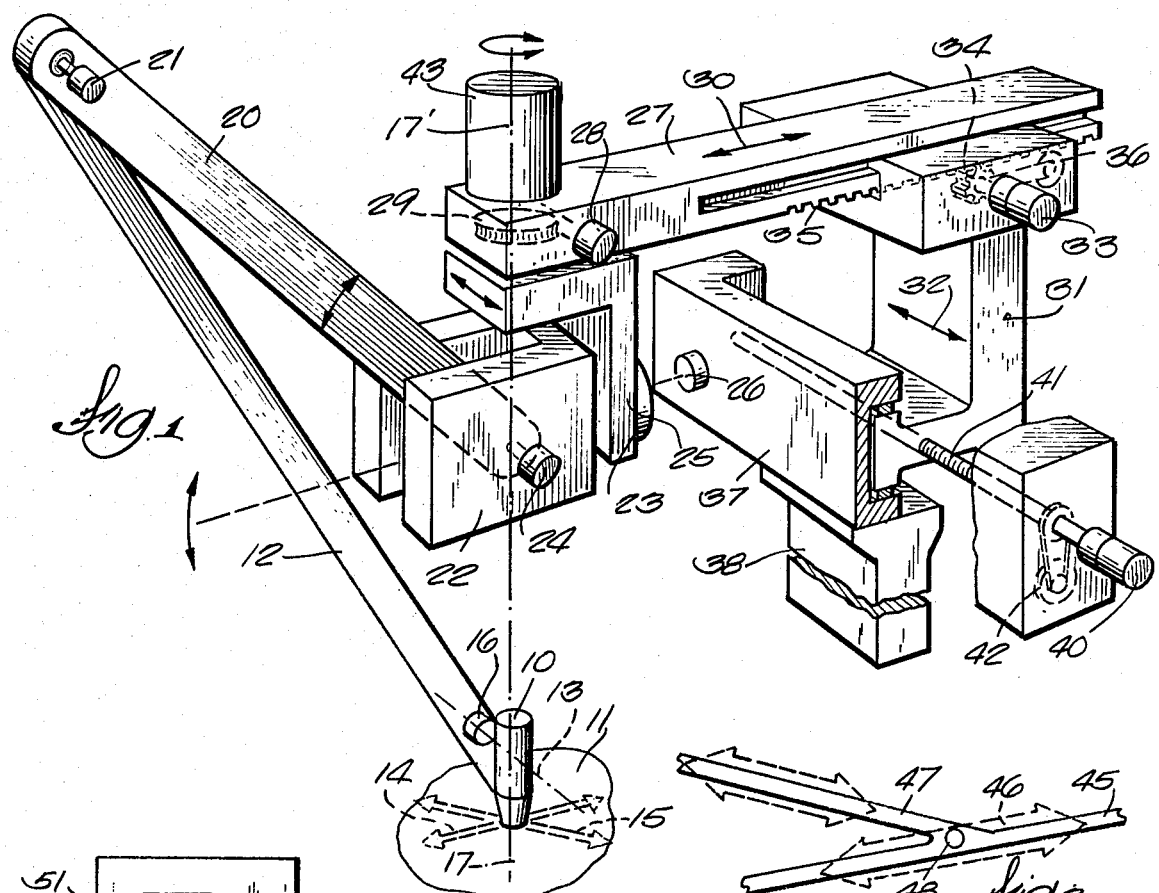
Fig. 1
Fig. 3
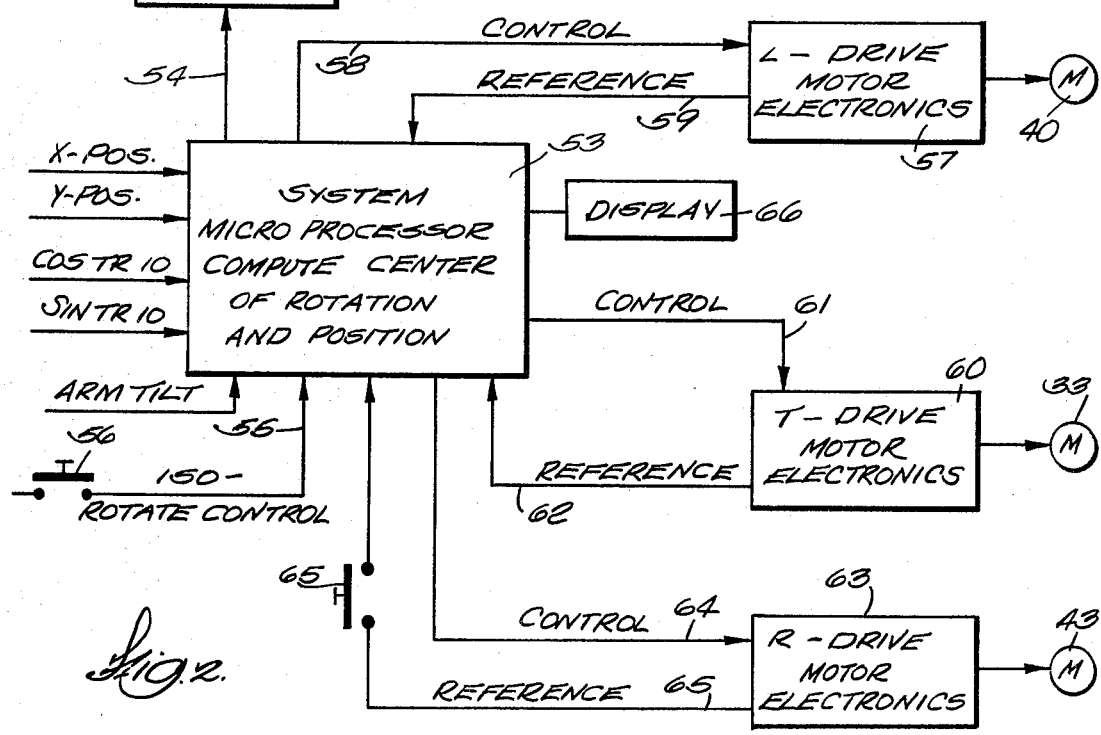
Fig. 2

DIAGNOSTIC ULTRASOUND APPARATUS HAVING AUTOMATIC ISOCENTRIC ROTATOR

This invention pertains to apparatus for examining bodies withe ultrasound and is prarticularly concerned with facilitating making B-scans at selected angles originating at a common point of intersection called the isocenter.

Typical diagnostic ultrasonic examination apparatus comprises a longitudinally movable carriage which has a transversely movable carriage or crossarm mounted on it. A so-called head is mounted on the free end of the transverse arm. The head has the properties of a gimbal in that it allows for rotation about vertical and horizontal axes. A first arm is pivotally connected to the head for rotating about a horizontal axis and a second arm is pivotally connected to the opposite end of the first arm. An ultrasonic transducer for projecting an ultrasonic beam and receiving echoes from anatomical parts is pivotally mounted on the free end of the second arm. In making a B-scan, the transducer is pushed along the body surface and the two arms move in a single vertical plane. Because the lengths of the arms and the angles between them are known and determined, respectively, the position of the transducer in the vertical plane can be and is computed. By knowing the position of the transducer, the location of all returning echoes becomes known so an image of a plane in the body can be formed by reconstructing the echoes in a display. Sometimes compound scans are made in which case the transducer is not only translated along the body but is rocked back and forth on its axis at the same time.

Since the anatomical part of interest is concealed in the body, several different scans might be necessary to find and display the anatomy of primary interest. Sometimes the operator wants to determine more exactly where superimposed anatomical parts cross over each other or wants to distinguish the disposition and configuration of anatomical parts which might otherewise be confused with sound echoes from other parts. In such cases the operator will scan the ultrasonic transducer transversely, for instance, to obtain an ulstasound image along one cross section of the body and then will be required to rotate the scanner about the vertical axis of the transducer while the axis remains directed through a particular point of interest. For instance, a blood vessel pattern may be under examination. The operator might scan along a particular blood vessel which has another vessel branching into or out of it and it is desired to obtain an image of where the junction occurs and the direction in which the branch vessel is disposed. In prior art apparatus, the operator would establish the transducer at the point where the vessel junction occurs and would then scan at a variety of angles from that point until the path of the intercepting vessel is found and an image of it is displayed.

In prior art apparatus, in order to make scans at a variety of angles from a common point or isocenter at a variety of angles between transverse and longitudinal, it has been necessary for the operator to find the branch point and hold the transducer over it while simultaneously attempting to shift the transverse and longitudinal arms until the vertical axis of rotation of the head which supports the two arms was directly over the vertical axis of the transducer. If the head and transducer vertical axes are not coincident, the transducer moves in an arc about the vertical axis of the head and the desired originating point for the variety of scans is lost. Operators have had great difficulty in attempting to hold the transducer over a fixed point with one hand while using the other hand to shift the longitudinal and transverse carriages around until the axes align. Moreover, the operator has to make a judgment or estimate as to whether the axes are aligned which can never be done with the precision required except by trial and error.

SUMMARY OF THE INVENTION

A primary object of the present invention is to provide means for automatically determining the isocenter of the transducer and its supporting head.

In accordance with the invention, the operator is simply required to hold the transducer with one or both hands over the isocenter or the point from which one or more scans at different angles are to originate. All essential movable components of the scanner assembly operate potentiometers which provide signals to a microprocessor which allows the later to determine the position or coordinates of the transducer as is done in prior art ultrasound scanners for the purpose of coordinating the echo signals with the readout or display. In accordance with the invention, however, the microprocessor then uses the transducer position information to determine where the head axis should be located for it to be coincident with the axis of the transducer. A closed loop servo system then drives the longitudinal carriage and transverse crossarm in such manner that the vertical transducer and head axes become aligned and the motion automatically stops and the isocenter is determined. Then, by manual or motor driven means, the operator can swing the head by pushing on the articulated arms to establish the arms in a new vertical plane for directing the transducer along a new angle originating at the isocenter.

How the foregoing and other more specific objects of the invention are achieved will be evident in the ensuing more detailed description of a preferred embodiment of the invention which will now be set forth in reference to the drawings.

DESCRIPTION OF THE DRAWINGS

FIG. 1 is a fragmentary perspective view of an ultrasonic scanner which incorporates the new automatic isocenter locator;

FIG. 2 is a block diagram which shows the electrical components which are involved in automatic isocenter determination; and FIG. 3 is a diagram of two intersecting blood vessels whose paths may be more easily determined with the present invention.

DESCRIPTION OF A PREFERRED EMBODIMENT

The ultrasound scanner shown in FIG. 1 comprises a transducer 10 whose lower end emits high frequency ultrasound into a body 11 and receives echoes from whereever there are impedance changes within the body. Transducer 10 is mounted at the distal end of an arm 12 for being pivoted optionally about an axis 13 in some types of B-scans and it is held vertically in other types of scans. One possible scanning path along body 11 might be the one indicated by the double arrowhead dashed line 14 and another among the many angularly related alternate paths is indicated by the double arrowheaded dashed line 15. The point or zone of intersection of lines 14 and 15 can be looked upon as being the isocenter and it is the object of the invention to enable making scans which all pass through or cross the isocenter. The isocentric axis is marked 17.

A potentiometer 16 is shown symbolically as being coaxial with transducer axis 13 and the potentiometer shaft, not shown, is turned when the transducer is turned on its axis. Actually, the potentiometer may be located remotely from the transducer and be driven by pulleys and cables, not shown. Potentiometer 16 is a conventional sine-cosine type which outputs two analog signals, one of which corresponds with the sine of the angle through which its shaft and, hence, the transducer shaft is rotated and the other of which corresponds with the cosine of this angle. Producing analog signals representative of the sine and cosine of an ultrasound transducer that is mounted on scanning arms is known per se. In accordance with the invention, however, this signal and some of the other signals are used for conventional purposes and for the novel purpose of assuring that isocentric rotation of the scanning arm is obtained.

Transducer supporting arm 12 in FIG. 1 is pivotally connected or articulated with another arm 20. In the vicinity of the pivot connection between arms 12 and 20, another sine-cosine potentiometer 21 is symbolized. This potentiometer is for enabling determination of the angular attitude of arm 12 which is part of the conventional process of determining the x and y coordinates of transducer 10 which, as is well-known, involves using the cosine function to get the sum of the x vectors and the sine function to get the sum of the y vectors of the transducer in relation to a reference point so that coordination between the transducer position and the image display can be obtained.

Arm 20 is pivotally mounted on a head assembly comprised of two parts, a yoke part 22 and an inverted L-shaped part 23. Pivoting of arm 20 on yoke 22 also results in another sine-cosine potentiometer 24 being driven coordinately for producing analog signals corresponding with the sine and cosine of the angle at which arm 20 is disposed relative to vertical and horizontal.

Yoke part 22 of the head is journaled for rotation or tilting about a horizontal axis on L-shaped part 23. The horizontal rotational axis of part 22 on part 23 is indicated by the dashed line 25. Another symbolically represented sine-cosine potentiometer 26 produces the analog signals which are indicative of the tilt angular position of part 22 and, hence, of coplanar arms 12 and 20. Arms 12 and 20 are constrained to swing in a common plane as a single elbowed arm but the plane can be tilted in either direction by rotation of yoke part 22 of the head abouts its axis 25.

The L-shaped part 23 of the head assembly is journaled for rotation about a vertical axis at the end of a transversely and reversibly movable arm 27. The vertical axis of L-shaped part 23 is indicated by the dashed line which is marked 17′. The object of the invention is to automatically make axis 17′ align with or become coincident with axis 17 through the transducer 10. If axes 17′ and 17 are not aligned, that is, if the transducer is offset laterally with respect to the vertical axis 17′, the transducer will describe an arc when the unitary articulated arms 12 and 20 are jointly swung to a new vertical plane and any scan taken in this orientation of the arms would not fall on a line that passes through the isocenter which is to say that other scans would not originate from a common point of intersection of the planes. The rotational angle of L-shaped part 23 of the head and, hence, arm 12, 20, is determined with a sine-cosine potentiometer 28 which is symbolically represented as being driven by a worm wheel 29 although in an actual case this potentiometer like the others, might be remotely located from its driving means and be driven with wires, cables and pulleys. The bidirectional movement of transversely translatable arm 27 is indicated by the double arrow-headed line 30.

Transversely movable arm 27 is mounted for translating in a longitudinally movable carriage 31 which is movable bidirectionally as indicated by the double arrowheaded line 32. Transverse arm 27 moves orthogonally to the longitudinally movable carriage. Longitudinally movable carriage has a motor 33 mounted on it. The motor has a pinion 34 which engages with a gear rack 35 on transverse arm 27 for driving the latter in and out as is self-evident. A linear potentiometer 36 provides an analog signal which allows determination of the distance from a reference point by which arm 27 is extended or retracted. This distance must be factored into calculating the X coordinate of the transducer 10. Potentiometer 36 may be driven by any suitable means such as a belt or cable drive.

Longitudinally movable carriage 31 is supported in a guide 37 which is fixedly mounted on a pedestal 38. This pedestal may be on a cart, not shown, which facilitates moving the ultrasound scanner to the most advantageous position relative to a patient. Longitudinal carriage 31 is driven by means of a reversible motor 40 which, in this example, turns a lead screw 41 that is threaded into carriage 31 for driving it longitudinally in stationary guide 37. The longitudinal position of carriage 31 is determined by analog signals derived from another linear potentiometer 42 which is symbolized as being driven directly from lead screw 41 by means of a belt.

Before discussing how the invention enables automatic achievement of isocentric rotation of coplanar arms 20 and 12 about the transducer axis and the axis which supports these arms, a typical case of using isocentric rotation will be discussed in connection with FIG. 3. FIG. 3 illustrates a blood vessel 45 which the operator may be tracing or following and displaying an image thereof by moving the transducer in the B-scan mode in one direction or the other as indicated by the double arrowheaded dashed line 46. Assume that the operator has crossed the junction of another blood vessel or branch 47 and desires to determine the direction in which it extends relative to vessel 45. If the operator observes on the image display that the junction seems to occur in the vicinity of the circle 48 the desire would be to scan in various directions across this circle to determine the direction in which the junctioning blood vessel 47 runs. The procedure involves running scans in opposite radial directions from circle 48, that is, the isocenter, until the vessel is found and displayed. As indicated earlier, in prior art apparatus, the operator would then tend to get the transducer axis 17 located in alignment with the vertical axis 17′ about which arm 20, 12 swings by using the manual heuristic approach to obtaining alignment by making a visual judgment followed by a scan and then making additional scans until it is evident that the true isocenter has been found. In accordance with the invention, the operator simply holds the transducer over the point that he wants to be considered the isocenter, activates the system and waits a moment for the transverse arm 27 and longitudinally movable carriage to be driven until axis 17' is aligned with axis 17. Then the operator may swing articulated coplanar arms 12 and 20 to any new vertical plane and proceed with a scan that will surely cross the isocenter. This is true even though articulated arms 12 and 20 are tilted away from vertical as a result of rotating them jointly about the tilting horizontal axis 25 on which yoke part 22 of the head assembly rotates.

Although not previously mentioned, it should be noted that L-shaped part 23 of the head is subject to power rotation about vertical axis 17' under the influence of a motor 43 which is mounted on arm 27. In accordance with the invention, head part 22 and, hence, articulated arms 12 and 20 may be turned manually about axis 17' or, as in the illustrated embodiment, may be turned with motor 43.

FIG. 2 shows a block diagram of the main components of a diagnostic ultrasound system including the new means for automatically driving the scanner head to the isorotate position. Block 50 represents a conventional image display system including the ultrasound data processing electronics and a cathode ray tube display screen 51. Input of ultrasound echo signals is symbolized by the arrowheaded line 52. The position of the ultrasound echoes in the scanning format is determined by a microprocessor 53 which sends appropriate coordinating signals by way of a bus 54 to the display electronics in a conventional manner.

The analog signal from the various potentiometers which are used for determining the x and y coordinates of transducer 10 are converted to digital signals by means which are not shown and the digital position indicative signals are inputted to microprocessor 53 as symbolized by the two arrowheaded lines marked X-POS and Y-POS and are meant to indicate the signals which the microprocessor uses to determine the x and y positions or coordinates of the transducer 10 and, particularly, its axis 13. Using a microprocessor to determine the coordinates of a transducer is known in the prior ultrasonic equipment art. As has been done before, when the system is operating, data corresponding with the instantaneous x and y coordinates of the transducer is stored in the memory of the microprocessor system.

Other inputs to the microprocessor system are signals representative of the cosine and sine of the transducer angulation about its axis 13. These signals are derived from potentiometer 16. The signals are indicated by the arrowheaded lines labeled cos TR10 and sin TR10. An additional input signal to the microprocessor is the digital signal representative of the articulated arm 20, 12 tilt. This is the tilt of head part 22 about its axis 25 and the signal originates at potentiometer 26.

Another line leading into the microprocessor system is labeled isorotate control and is marked 55. It has a momentary contact switch 56 in it. Operation of this switch by the operator causes the scanner head to be driven to the position where its axis 17' coincides with the axis 17 of the transducer. As previously explained, the operator holds the transducer over the point which he wants to be the isocenter and, after operating switch 56, the microprocessor, using the x and y position data for the transducer head which it already has stored calculates where the scanning head should be to align its axis 17' vertically with transducer 17. When this position is rapidly calculated, transverse arm drive motor 33 and longitudinal drive motor 40 are energized and automatically drive arm 27 and carriage 31 to establish the head coaxial with the tranaducer. In FIG. 2, the servo system electronics for the longitudinal drive motor 40 are symbolized by the block marked 57 and labeled L-drive motor electronics. Line 58 is for delivering the control signal from the system microprocessor to the longitudinal drive motor electronics and line 59 is for the reference signal which tells the electronics how far it should drive the head in the longitudinal direction.

The servo system electronics for transverse drive motor 33 are in a block labeled T-drive motor electronics which block is also marked 60. Again there is a control line 61 from the microprocessor which activates the motor electronics to drive motor 33 and there is a reference signal on line 62 which tells the electronics when to stop driving.

The servo system electronics for the isocenter rotator motor 43 is represented by a block marked 63 and labeled R-drive motor electronics. It has a control line 64 and a reference line 65 as is the case with the other controls. Besides driving the head longitudinally and transversely as required to position the axis of the head coincident with the axis of the transducer in response to the isorotate control switch 56 being operated, the operator is given control over the new plane in which arms 12, 20 will move for a scan of the transducer through the isocenter, another switch 65 is provided for inputting a signal which tells the isorotator motor 43 how far it should drive for the next desired scan. The operator can determine the angle at which the articulated arm 12, 20 is oriented about the transducer vertical axis by viewing a digital display 66 which provides a readout of the angle. In the alternative, the angle could be displayed by suitable graphics directly on cathode ray tube display 51. Instead of power driven rotation of the scanner arms 12, 20 after isocenter is achieved, the system can also be implemented with a switch, not shown, that causes motor 43 to unclutch or disengage so that the articulated arm can be rotated manually if desired.

We claim:

1. Apparatus for making ultrasound examinations of a body including carriage means mounted for moving longitudinally in the Y direction, an arm mounted on said carriage means for moving transversely in the x direction, a head mounted on said transversely movable arm for turning about a vertical axis, an articulated arm composed of pivotally connected arm sections one of which is pivotally mounted to said head and another of which has an ultrasound transducer pivotally mounted on it, said articulated arm being constrained to move in a single plane to scan said transducer along a single plane through a body and said articulated arm being swingable with said head about said vertical axis to enable selection of the scanning plane of said arm and transducer, and the improvement for automatically establishing said vertical axis about which said articulated arm swings at the same X and Y coordinates at which said transducer is located when it is over a selected isocenter on the body so said articulated arm can be swung to a selected plane without translating said transducer from said isocenter, comprising:

first motor means operable to translate said transversely movable arm in reverse directions and controller means for said motor means, second motor means operable to translate said longitudinally movable carriage means in reverse directions to thereby shift said transversely movable arm longitudinally and controller means for said second motor means, means for providing signals representative of the X coordinate and Y coordinate position of said transducer, processor means having input means for said signals and being operative to use said signals to activate said controller means to cause said respective motor means to move said transversely movable arm and carriage means until said vertical axis about which said articulated arm swings has the same X and Y coordinates as said transducer, and a circuit including a switch operable to cause said motor controllers to be activated.

2. The apparatus as in claim 1 including a third motor means operative to drive said head about said vertical axis for swinging said arm to a desired plane passing through said isocenter and controller means for said third motor means, a circuit including a switch operable to activate said controller for said third motor to cause said motor to drive until said arm is angulated to the desired plane.

3. The apparatus as in claim 2 including means controlled by said processor means for displaying the coordinates of the isocenter.

* * * * *